United States Patent
Petersson

(10) Patent No.: US 9,254,296 B2
(45) Date of Patent: Feb. 9, 2016

(54) PHARMACEUTICAL COMPOSITION COMPRISING VITAMIN D ANALOGUE AND COSOLVENT-SURFACTANT MIXTURE

(75) Inventor: Karsten Petersson, Ballerup (DK)

(73) Assignee: LEO PHARMA A/S, Ballerup (DK)

( * ) Notice: Subject to any disclaimer, the term of this patent is extended or adjusted under 35 U.S.C. 154(b) by 0 days.

(21) Appl. No.: 13/518,333

(22) PCT Filed: Dec. 22, 2009

(86) PCT No.: PCT/DK2009/000266
§ 371 (c)(1),
(2), (4) Date: Aug. 17, 2012

(87) PCT Pub. No.: WO2011/076206
PCT Pub. Date: Jun. 30, 2011

(65) Prior Publication Data
US 2013/0005680 A1    Jan. 3, 2013

(51) Int. Cl.
| | |
|---|---|
| A61K 31/593 | (2006.01) |
| A61K 31/592 | (2006.01) |
| A61K 31/7016 | (2006.01) |
| A61P 17/00 | (2006.01) |
| A61P 17/06 | (2006.01) |
| A61P 17/08 | (2006.01) |
| A61P 17/10 | (2006.01) |
| A61K 45/06 | (2006.01) |
| A61K 9/00 | (2006.01) |
| A61K 47/10 | (2006.01) |
| A61K 47/14 | (2006.01) |
| A61K 47/26 | (2006.01) |
| A61K 9/113 | (2006.01) |
| A61K 47/44 | (2006.01) |

(52) U.S. Cl.
CPC ............ *A61K 31/592* (2013.01); *A61K 9/0014* (2013.01); *A61K 9/113* (2013.01); *A61K 31/593* (2013.01); *A61K 31/7016* (2013.01); *A61K 45/06* (2013.01); *A61K 47/10* (2013.01); *A61K 47/14* (2013.01); *A61K 47/26* (2013.01); *A61K 47/44* (2013.01)

(58) Field of Classification Search
CPC ..... A61K 31/593; A61K 47/44; A61K 9/113; A61K 47/26; A61K 47/14; A61K 47/10; A61K 31/592; A61K 45/06; A61K 31/7016; A61K 9/0014; A61K 2300/00
USPC .................................................. 514/53, 167
See application file for complete search history.

(56) References Cited

U.S. PATENT DOCUMENTS

| | | | |
|---|---|---|---|
| 5,985,177 A | 11/1999 | Yoshida et al. | |
| 5,990,100 A | 11/1999 | Rosenberg et al. | |
| 6,432,422 B1 * | 8/2002 | Yasukawa et al. | 424/401 |
| 6,787,529 B2 * | 9/2004 | Høy et al. | 514/167 |
| 7,262,158 B1 * | 8/2007 | Lukenbach et al. | 510/122 |
| 2006/0292080 A1 | 12/2006 | Abram et al. | |
| 2008/0234239 A1 * | 9/2008 | Wheeler et al. | 514/167 |
| 2008/0293681 A1 | 11/2008 | Willcox et al. | |
| 2009/0298801 A1 | 12/2009 | Willcox et al. | |

FOREIGN PATENT DOCUMENTS

| | | |
|---|---|---|
| EP | 1040832 A1 | 10/2000 |
| EP | 1051974 A1 | 11/2000 |
| JP | 2001-25359 A | 1/2001 |
| JP | 2008-13515 A | 1/2008 |
| WO | WO 94/15912 A1 | 7/1994 |
| WO | WO 2006/131401 A2 | 12/2006 |
| WO | WO 2006/138056 A1 | 12/2006 |
| WO | WO 2008/095796 A1 | 8/2008 |

OTHER PUBLICATIONS

Catanzaro et al., "Propylene glycol dermatitis", Journal of the American Academy of Dermatology, vol. 24, No. 1, Jan. 1991, pp. 90-95.
Djekic et al., "The influence of cosurfactants and oils on the formation of pharmaceutical microemulsions based on PEG-8 caprylic/capric glycerides", Int J. Pharm, vol. 352 (1-2): 231-9, Mar. 20, 2008, Epub Nov. 4, 2007, 2 pages provided.
Hannuksela et al., "Skin reactions to propylene glycol", Contact Dermatitis, vol. 1, 1975, pp. 112-116.
Kragballe et al., "Efficacy and safety of calcipotriol plus betamethasone dipropionate scalp formulation compared with calcipotriol scalp solution in the treatment of scalp psoriasis: a randomized controlled trial", British Journal of Dermatology, vol. 161, 2009, pp. 159-166.

* cited by examiner

*Primary Examiner* — Anoop Singh
*Assistant Examiner* — Doan Phan
(74) *Attorney, Agent, or Firm* — Birch, Stewart, Kolasch & Birch, LLP

(57) ABSTRACT

A topical pharmaceutical composition which is an oil-in-water-oil emulsion comprising a vitamin D derivative or analogue dissolved in a mixture of a non-ionic surfactant and a lower alkanol. The topical pharmaceutical composition may be used in the treatment of dermal conditions, such as psoriasis.

28 Claims, 6 Drawing Sheets

Figure 1    Solubility of Calcipotriol, μg/g, in aqueous vehicles using cetomacrogol 1000 as surfactant, and ethanol as co-solvent at 25°C.
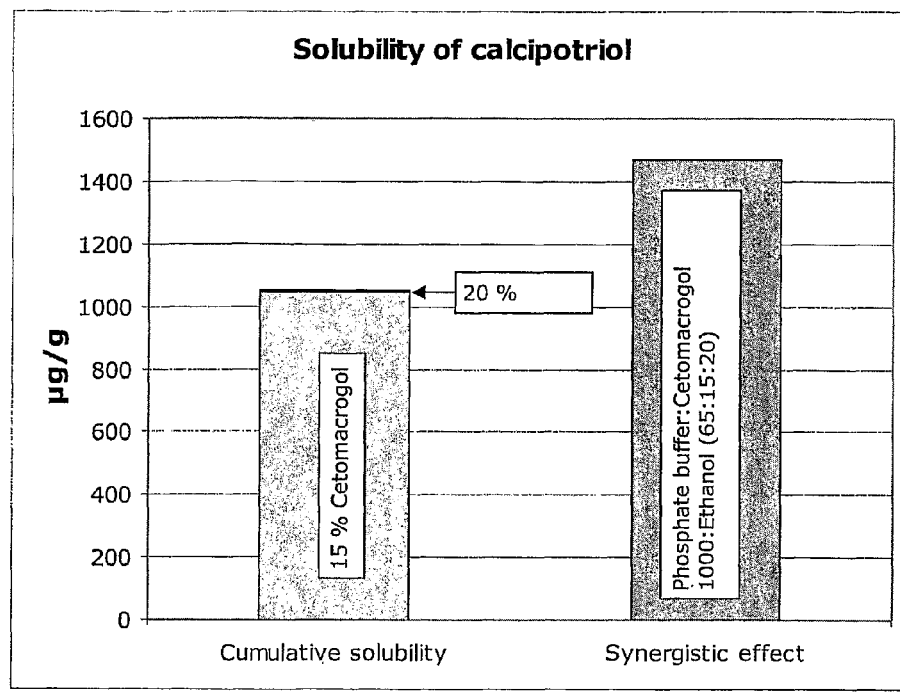

Figure 2  Solubility of Calcipotriol, μg/g, in aqueous vehicles using Labrasol as surfactant, and ethanol as co-solvent at 25°C.
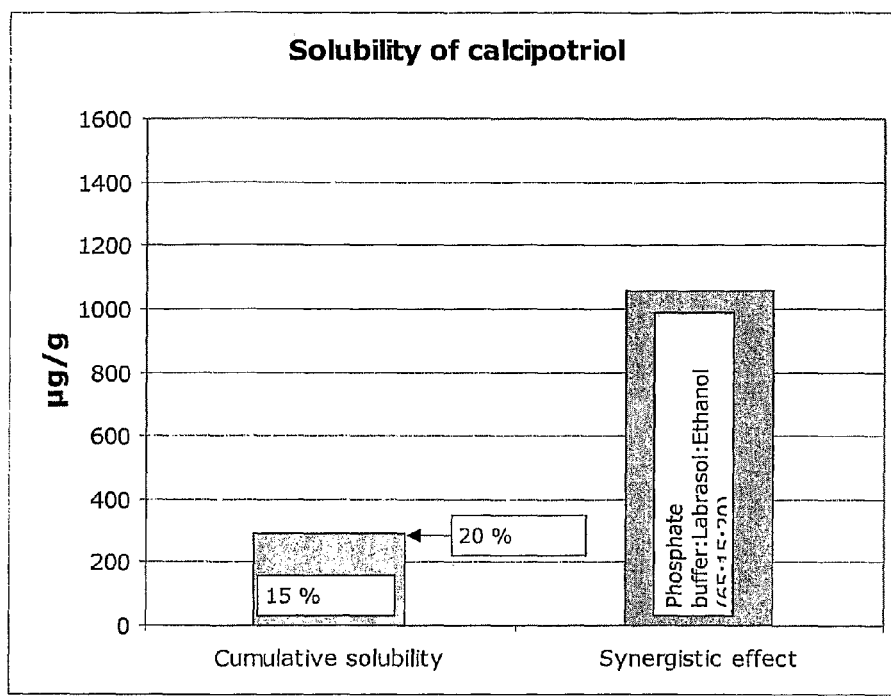

Figure 3  Solubility of Calcipotriol, μg/g, in aqueous vehicles using Labrasol as surfactant, and isopropanol as co-solvent at 25°C.
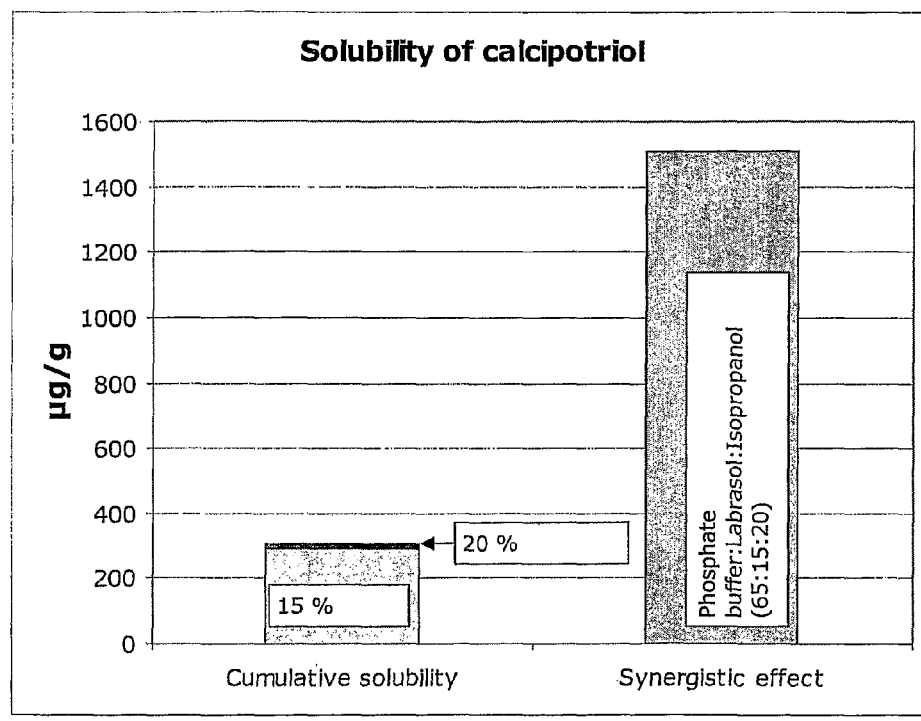

Figure 4   Solubility of Calcipotriol, µg/g, in aqueous vehicles using Tween 80 as surfactant, and ethanol as co-solvent at 25°C.
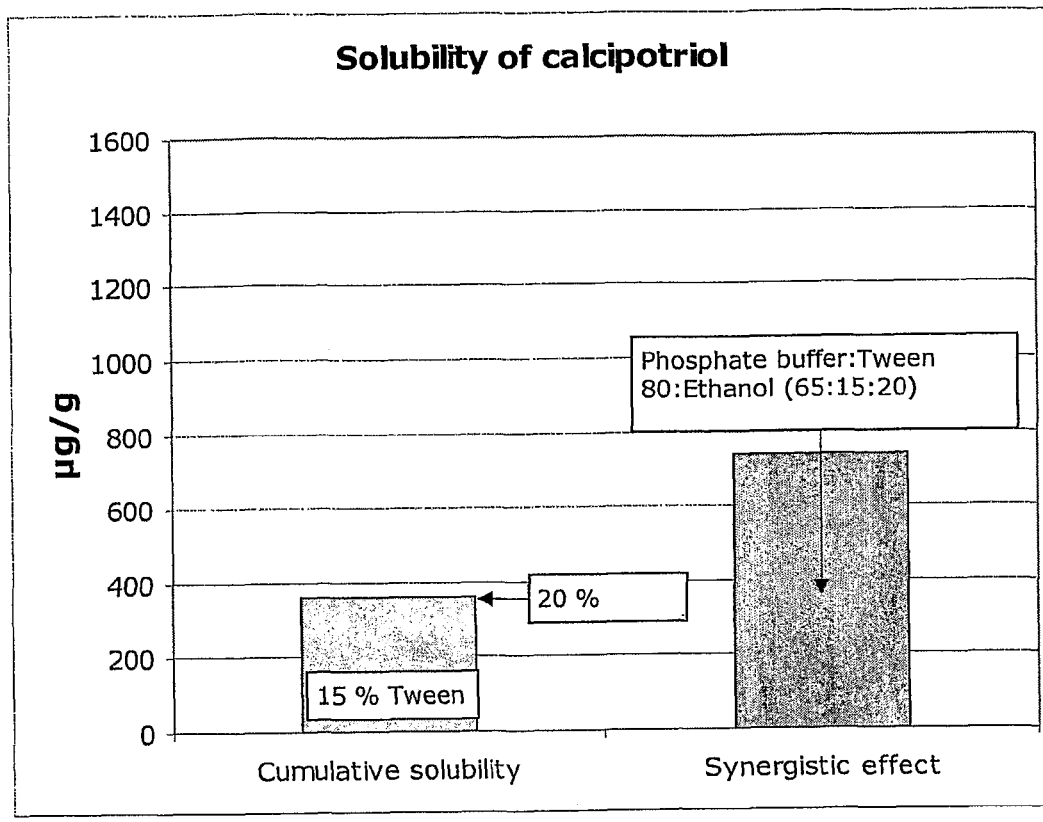

PHARMACEUTICAL COMPOSITION COMPRISING VITAMIN D ANALOGUE AND COSOLVENT-SURFACTANT MIXTURE

FIELD OF THE INVENTION

The present invention relates to a topical pharmaceutical composition for cutaneous application comprising a pharmacologically active agent, a surfactant, a co-solvent and an aqueous phase.

BACKGROUND OF THE INVENTION

Psoriasis is a chronic inflammatory skin disease that manifests as erythematous, dry, scaling plaques resulting from hyperkeratosis. The plaques are most often found on the elbows, knees and scalp, though more extensive lesions may appear on other parts of the body, notably the lumbosacral region. The most common treatment of mild to moderate psoriasis involves topical application of a composition containing a corticosteroid as the active ingredient. While efficacious, corticosteroids have the disadvantage of a number of adverse effects such as skin atrophy, striae, acneiform eruptions, perioral dermatitis, overgrowth of skin fungus and bacteria, hypopigmentation of pigmented skin and rosacea.

For many years, however, an advantageous non-steroidal treatment of psoriasis has consisted in topical treatment with the vitamin D analogue compound, calcipotriol, formulated in an ointment composition (marketed as Daivonex® or Dovonex® ointment by LEO Pharma) in which the calcipotriol is present in solution or a cream composition (marketed as Daivonex® or Dovonex® cream by LEO Pharma). The solvent in the ointment composition is propylene glycol which has the advantage of enhancing penetration of the active ingredient into the skin, leading to an improved efficacy, but which is also known to act as a skin irritant. Thus, it has been reported that the inclusion of propylene glycol in topical compositions frequently causes patients to develop contact dermatitis (one study reported a number of irritant reactions to propylene glycol of 12.5%, cf. M. Hannuksela et al., *Contact Dermatitis* 1, 1975, pp. 112-116), and the number of irritant reactions increases when propylene glycol is used in high concentrations (as reviewed by J. Catanzaro and J. Graham Smith, *J. Am. Acad. Dermatol.* 24, 1991, pp. 90-95). Due to the improved penetration of calcipotriol into the skin resulting, inter alia, from the presence of propylene glycol, Daivonex® ointment has been found to be more efficacious in the treatment of psoriatic lesions than Daivonex® cream, but has also caused skin irritation in a significant proportion of psoriasis patients.

It is therefore an object of the invention to provide a topical composition comprising a vitamin D derivative or analogue as the active ingredient, which has skin penetration and biological activity properties comparable to those of Daivonex® ointment, but which does not contain propylene glycol as the solvent.

SUMMARY OF THE INVENTION

Human skin, in particular the outer layer, the stratum corneum, provides an effective barrier against penetration of microbial pathogens and toxic chemicals. While this property of skin is generally beneficial, it complicates the dermal administration of pharmaceuticals in that a large quantity, if not most, of the active ingredient applied on the skin of a patient suffering from a dermal disease may not penetrate into the viable layers of the skin where it exerts its activity. To ensure an adequate penetration of the active ingredient to the dermis and epidermis, it is generally preferred to include the active ingredient in a dissolved state, typically in the presence of a solvent in the form of an alcohol, e.g. ethanol, or diol, e.g. propylene glycol. Propylene glycol is a well-known penetration enhancer, i.e. a substance which is capable of penetrating the stratum corneum and "draw" low-molecular components such as therapeutically active components in the vehicle into the epidermis. Propylene glycol may in itself give rise to significant skin irritation, and it is also capable of "drawing" low-molecular and potentially irritative components of the vehicle into the epidermis, leading to an overall irritative effect of conventional vehicles including propylene glycol. For this reason, the presence of propylene glycol as a solvent in compositions intended for the treatment of inflammatory skin diseases may exacerbate the inflammatory response.

In the research leading to the present invention, it was an object to identify a solvent combination which is more effective to dissolve a sparingly soluble compound such as a vitamin D analogue than low-molecular alcohols or diols when used on their own as co-solvents in admixture with an aqueous phase, and which in addition comprises a significantly lower amount of the low-molecular alcohol co-solvent. It has surprisingly been found that mixing certain surfactants with certain lower alkanols provides mixtures with an exceptionally high solubilization capacity. The resulting composition where the individual solvent components act synergistically resulting in a satisfactory penetration of the vitamin D derivative or analogue thereof into the viable layers of the skin at a lower concentration of co-solvent than when an alcohol or diol alone is used as the co-solvent. Furthermore, compositions of the invention exhibit a comparable or higher biological activity to that of Daivonex® ointment as determined in the target gene activation assay described in Example 4 below. In addition, the composition is physically stable, and the vitamin D analogue is chemically stable therein.

Accordingly, the present invention relates to a topical composition for cutaneous application which is an oil-in-water-in-oil emulsion comprising an aqueous phase containing, dispersed therein, a lipophilic phase comprising
(a) a vitamin D derivative or analogue in dissolved form;
(b) a non-ionic surfactant selected from the group consisting of polyoxyl glycerides, polyoxyethylene castor oil derivatives, polyoxyethylene alkyl ethers, polysorbates or poloxamers; and
(c) a lower alkanol co-solvent;
said aqueous phase being dispersed in a pharmaceutically acceptable anhydrous lipophilic carrier or vehicle.

In another aspect, the invention relates to a topical composition as described herein for use in the prevention or treatment of dermal diseases or conditions.

BRIEF DESCRIPTION OF THE DRAWINGS

FIGS. 1-4 are graphs showing the solubility of calcipotriol monohydrate in co-solvent-surfactant mixtures included in the present composition compared to the solubility of calcipotriol monohydrate in either the co-solvent or the surfactant alone.

DETAILED DESCRIPTION OF THE INVENTION

Definitions

Figure 5A:
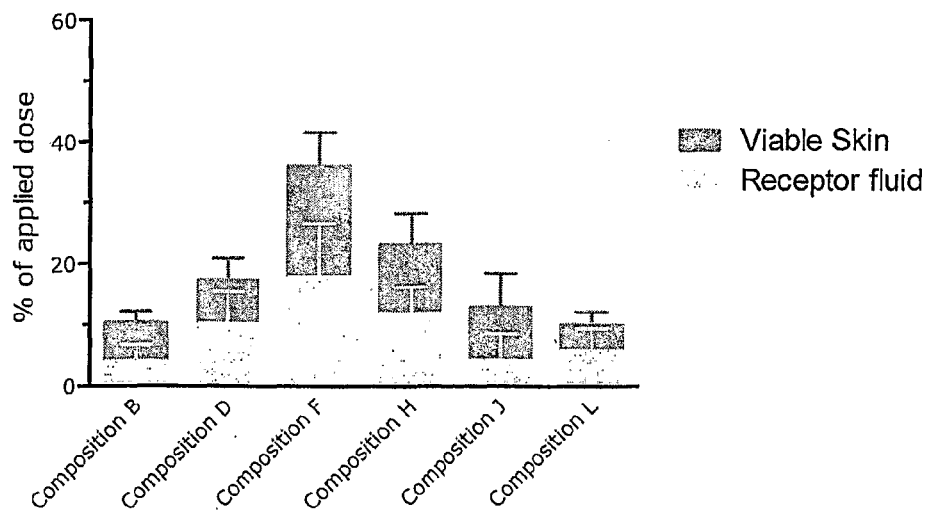
FIGS. 5a and 5b are graphs showing the penetration into the skin of composition of the invention.

In the present context, the term "non-ionic surfactant" is intended to indicate a surfactant comprising a hydrophilic and a hydrophobic portion in which the hydrophilic portion carries no charge but derives its surface activity from highly polar groups such as polyoxyethylene groups. For the present purpose, the surfactant is an oil-in-water surfactant with an HLB value of 9-18.

The term "lower alkanol co-solvent" is intended to indicate a solvent consisting essentially of a $C_{1-6}$ straight or branched alkanol, e.g. methanol, ethanol, propanol, isopropanol or butanol.

The term "vitamin D derivative" is intended to indicate a biologically active metabolite of vitamin $D_3$, such as calcitriol, or a precursor to such a metabolite, such as alfacalcidol.

The term "vitamin D analogue" is intended to indicate a synthetic compound comprising a vitamin D scaffold with sidechain modifications and/or modifications of the scaffold itself.

The analogue exhibits a biological activity on the vitamin D receptor comparable to that of naturally occurring vitamin D compounds.

"Calcipotriol" is a vitamin D analogue of the formula

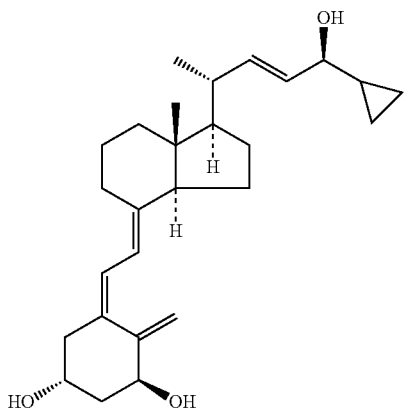

Calcipotriol has been found to exist in two crystalline forms, an anhydrate and a monohydrate. Calcipotriol monohydrate and its preparation are disclosed in WO 94/15912.

The term "storage stability" is intended to indicate that the composition exhibits chemical and physical stability characteristics that permit storage of the composition, at refrigeration or, preferably, room temperature for a sufficient period of time to make the composition commercially viable, such as at least 12 months, in particular at least 18 months, and preferably at least 2 years.

The term "chemical stability" or "chemically stable" is intended to indicate that no more than 10%, preferably no more than 5%, of the vitamin D derivative or analogue degrades over the shelf-life of the product, typically 2 years. An approximation of chemical stability at room temperature is obtained by subjecting the composition to accelerated stability studies at 40° C. If less than about 10% of the substance has degraded after 3 months at 40° C., this is usually taken to correspond to a shelf-life of 2 years at room temperature. In particular with respect to calcipotriol, "chemical stability" is intended to mean that the calcipotriol does not degrade significantly over time to 24-epi calcipotriol or other degradation products of calcipotriol in the finished pharmaceutical product.

The term "physical stability" or "physically stable" is intended to mean that the composition retains its macroscopic and microscopic appearance over the shelf-life of the product, e.g. that the vitamin D derivative or analogue does not precipitate from the solvent phase or that there is no visible phase separation of the solvent phase and the carrier phase.

The term "substantially anhydrous" is intended to mean that the content of free water in the lipophilic carrier or vehicle does not exceed about 2% by weight, preferably not about 1% by weight, of the carrier or vehicle.

The term "solubilization capacity" is intended to indicate the ability of a solvent or mixture of solvents to dissolve a given substance, expressed as the amount required to effect complete solubilization of the substance.

The term "synergistic(ally)" is intended to imply that the solubility of the vitamin D derivative or analogue is significantly higher, in some instances several fold higher, when a combination of co-solvent and surfactant is present in the aqueous phase than the sum of solubilities in either the co-solvent or the surfactant when these are added individually to the aqueous phase.

The term "skin penetration" is intended to mean the diffusion of the active ingredient into the different layers of the skin, i.e. the stratum corneum, epidermis and dermis.

The term "skin permeation" is intended to mean the flux of the active ingredient through the skin into the systemic circulation or, in case of in vitro studies such as those reported in Example 3 below, the receptor fluid of the Franz cell apparatus used in the experiment.

The term "biological activity" is intended to mean the activity of a vitamin D derivative or analogue when applied to skin in a composition of the invention. The biological activity of compositions is determined in an in vitro assay measuring the activation of a target gene encoding cathelicidin in a reconstructed human epidermis model involving cultured human keratinocytes, as described in detail in Example 5 below.

Embodiments of the Invention

In an embodiment of the invention, the composition comprises a vitamin D derivative or analogue selected from the group consisting of calcipotriol, calcitriol, tacalcitol, maxacalcitol, paricalcitol and alfacalcidol. In a currently favoured embodiment, the composition comprises calcipotriol or calcipotriol monohydrate as the vitamin D analogue.

In the present composition, the surfactant is generally present in a concentration of from about 0.5% by weight to about 5% by weight, or from about 1% by weight to about 3% by weight, or from about 1.2% by weight to about 2% by weight, such as about 1.5% by weight, of the composition.

According to the invention, the non-ionic surfactant is preferably selected from the group consisting of polyethylene glycol 8 caprylic/capric glyceride (a polyethylene glycol derivative of a mixture of mono-, di- and triglycerides of caprylic and capric acids with an average of 8 moles of ethylene oxide) or polyethylene glycol 6 caprylic/capric glyceride (a polyethylene glycol derivative of a mixture of mono-, di- and triglycerides of caprylic and capric acids with an average of 6 moles of ethylene oxide). The non-ionic surfactant is favourably polyethylene glycol 8 caprylic/capric glyceride, e.g. available from Gattefossé under the trade name Labrasol or from Condea under the trade name Softigen 767.

The non-ionic surfactant may also preferably be a polyethylene glycol $C_{6-20}$ fatty acid glyceride selected from the group consisting of caprylocaproyl PEG glyceride, lauroyl PEG glyceride, linoeoyl PEG glyceride, oleoyl PEG glyceride and stearoyl PEG glyceride, a polyoxyethylene $C_{8-20}$ alkyl ether selected from the group consisting of PEG monocetyl ether, PEG monolauryl ether, PEG monooleyl ether and PEG monostearyl ether, a polysorbate selected from the group consisting of polysorbate 20, 40, 60 and 80, a poloxamer selected from the group consisting of poloxamer 124, 237, 338 and 407, or a polyoxyethylene castor oil derivative such as polyoxyl castor oil or hydrogenated polyoxyl castor oil.

As indicated above, the composition further comprises a lower alkanol co-solvent which may favourably be selected from the group consisting of methanol, ethanol, n-propanol, isopropanol, n-butanol or 2-butanol. It has surprisingly been found that the amount of lower alkanol required to completely dissolve the vitamin D derivative or analogue may be substantially reduced (e.g. 2-5 fold reduced) in the presence of the surfactant compared to the amount required when the lower alkanol is used alone as a solvent. The lower alkanol co-solvent may favourably be present in a concentration of about 0.5-5%, in particular about 1-3%, or about 2%, by weight of the composition.

In a currently favoured embodiment, the co-solvent is ethanol and the non-ionic surfactant is polyethylene glycol 8 caprylic/capric glyceride, polysorbate 80 or PEG monocetyl ether, or the co-solvent is isopropanol and the non-ionic surfactant is polyoxyl castor oil, polyethylene glycol 8 caprylic/capric glyceride or polysorbate 80.

The ointment carrier may be a hydrocarbon or mixture of hydrocarbons with chain lengths ranging from $C_5$ to $C_{60}$. A frequently used ointment carrier is petrolatum, or white soft paraffin, which is composed of hydrocarbons of different chain lengths peaking at about $C_{40-44}$, or a mixture of petrolatum and liquid paraffin (consisting of hydrocarbons of different chain lengths peaking at $C_{28-40}$). While petrolatum provides occlusion of the treated skin surface, reducing transdermal loss of water and potentiating the therapeutic effect of the active ingredient in the composition, it tends to have a greasy and/or tacky feel which persists for quite some time after application, and it is not easily spreadable. It may therefore be preferred to employ paraffins consisting of hydrocarbons of a somewhat lower chain length, such as paraffins consisting of hydrocarbons with chain lengths peaking at $C_{14-16}$ $C_{18-22}$, $C_{20-22}$, $C_{26}$ or mixtures thereof (the hydrocarbon composition of the paraffins has been determined by gas chromatography). It has been found that such paraffins are more cosmetically acceptable in that they are less tacky and/or greasy on application and more easily spreadable. They are therefore expected to result in improved patient compliance. Suitable paraffins of this type, termed petrolatum jelly, are manufactured by Sonneborn and marketed under the trade name Sonnecone, e.g. Sonnecone CM, Sonnecone DM1, Sonnecone DM2 and Sonnecone HV. These paraffins are further disclosed and characterized in WO 2008/141078 which is incorporated herein by reference.

To impart a desired viscosity to the present composition, it may suitably include a lipophilic viscosity-increasing ingredient such as a wax. The wax may be a mineral wax composed of a mixture of high molecular weight hydrocarbons, e.g. saturated $C_{35-70}$ alkanes, such as microcrystalline wax. Alternatively, the wax may be a vegetable or animal wax, e.g. esters of $C_{14-32}$ fatty acids and $C_{14-32}$ fatty alcohols, such as beeswax. The amount of viscosity-increasing ingredient may vary according to the viscosifying power of the ingredient, but may typically be in the range of about 1-20% by weight of the composition. When the viscosity-increasing ingredient is microcrystalline wax it is typically present in an amount in the range of about 5-15% by weight, e.g. about 10% by weight, of the composition.

The composition may additionally comprise an emollient which may act to soften the thickened epidermis of the psoriatic plaques. A suitable emollient for inclusion in the present composition may be a silicone wax or a volatile silicone oil as the presence of silicone has additionally been found to aid penetration of calcipotriol into the skin. Compositions including a silicone have also been found to result in less skin irritation. Suitable silicone oils for inclusion in the present composition may be selected from cyclomethicone, dimethicone.

The amount of silicone oil included in the present composition is typically in the range of from about 1 to about 10% by weight, e.g. about 5% by weight, of the composition.

In Daivonex® ointment, the presence of propylene glycol is believed to be a major contributor to the skin irritation experienced by many patients. However, it has been found that calcipotriol may in itself be mildly irritative in some patients (A. Fullerton and J. Serup, Br. J. Dermatol. 137, 1997, pp. 234-240 and A. Fullerton et al., Br. J. Dermatol. 138, 1998, pp. 259-265). It may therefore be advantageous to include an anti-irritant compound in the present composition, such as glycerol, butylene glycol, sorbitol, sucrose, saccharin, menthol or nicotinamide. Glycerol has been described as a substance that is capable of protecting the skin against irritative substances (J. Bettinger et al., Dermatology 197, 1998, pp. 18-24) and has been found by us to reduce the release of IL-1α in a dose-dependent manner: thus, it has been found that the presence of 15% by weight of glycerol in a calcipotriol ointment results in a significantly lower level of release of IL-1α than does the inclusion of 10% by weight of glycerol which, in turn, results in a significantly lower level of IL-1α release than does the inclusion of 5% by weight of glycerol.

However, in addition to the anti-irritative effect, it has surprisingly been found that glycerol is capable of potentiating the biological activity of calcipotriol in that the expression of cathelicidin (in the assay described in Example 4 below) has been found to be increased with decreasing amounts of glycerol in the composition (i.e. more cathelicidin is expressed when the amount of glycerol is 5% by weight than when the amount of glycerol is 10% or 15%, respectively): this implies that with respect to inclusion of glycerol a balance has to be struck between a favourable anti-irritative effect and a favourable potentiating effect. We have found that the inclusion of about 5-10% by weight of glycerol in the present composition results in a significant anti-irritative effect as well as a significant potentiation of the biological activity of calcipotriol.

Calcipotriol is known to be a substance which is extremely sensitive to acid conditions (pH below about 7.0 in aqueous compositions or acidic reacting substances in non-aqueous compositions) which contribute to the rapid degradation of calcipotriol. To ensure an adequate chemical stability of the substance throughout the shelf-life of the composition, it may be advisable to include a compound capable of neutralizing acidic impurities which may be present in one or more of the excipients of the composition and which are detrimental to the chemical stability of calcipotriol. The acid neutralizing compound may favourably be selected from a buffer such as a phosphate buffer which may be included in an amount of about 0.025-0.1% by weight of the composition. The acid neutralizing compound may also be an amine such as triethanolamine, trometamol, monoethanolamine or diethanolamine, which may be included in the composition in an amount of about 0.1-2% by weight.

To maintain good physical stability of the composition, in particular to avoid separation of the aqueous and lipid phases therein, it may be advantageous to include a water-in-oil emulsifier with an HLB value of 3-8. Examples of such emulsifiers are polyoxyethylene $C_{8-22}$ alkyl ethers, e.g. polyoxyethylene stearyl ether, polyoxyethylene cetyl ether or polyoxyethylene lauryl ether.

The amount of water in the composition may range from about 1% to about 15% by weight, e.g. from about 5% to about 10% by weight, of the composition.

In a specific embodiment, the present composition comprises

| | |
|---|---|
| 0.003-0.008% w/w | calcipotriol (as monohydrate) |
| 1-3% w/w | polyethylene glycol 8 caprylic/capric glyceride |
| 1-3% w/w | ethanol |
| 3-8% w/w | polyoxyethylene stearyl ether |
| 5-10% w/w | water |
| 80-93% w/w | paraffin carrier. |

In another embodiment, the present composition comprises

| | |
|---|---|
| 0.003-0.008% w/w | calcipotriol (as monohydrate) |
| 1-3% w/w | polysorbate 80 |
| 1-3% w/w | ethanol |
| 3-8% w/w | polyoxyethylene stearyl ether |
| 5-10% w/w | water |
| 80-93% w/w | paraffin carrier. |

In a further embodiment, the composition comprises

| | |
|---|---|
| 0.003-0.008% w/w | calcipotriol (as monohydrate) |
| 1-3% w/w | polyethylene glycol monocetyl ether |
| 1-3% w/w | ethanol |
| 3-8% w/w | polyoxyethylene stearyl ether |
| 5-10% w/w | water |
| 80-93% w/w | paraffin carrier. |

In a still further embodiment, the present composition comprises

| | |
|---|---|
| 0.003-0.008% w/w | calcipotriol (as monohydrate) |
| 1-3% w/w | polyethylene glycol 8 caprylic/capric glyceride |
| 1-3% w/w | isopropanol |
| 3-8% w/w | polyoxyethylene stearyl ether |
| 5-10% w/w | water |
| 80-93% w/w | paraffin carrier. |

In a still further embodiment, the present composition comprises

| | |
|---|---|
| 0.003-0.008% w/w | calcipotriol (as monohydrate) |
| 1-3% w/w | polyoxyl castor oil |
| 1-3% w/w | isopropanol |
| 3-8% w/w | polyoxyethylene stearyl ether |
| 5-10% w/w | water |
| 80-93% w/w | paraffin carrier. |

In a still further embodiment, the present composition comprises

| | |
|---|---|
| 0.003-0.008% w/w | calcipotriol (as monohydrate) |
| 1-3% w/w | polysorbate 80 |
| 1-3% w/w | isopropanol |
| 3-8% w/w | polyoxyethylene stearyl ether |
| 5-10% w/w | water |
| 80-93% w/w | paraffin carrier. |

The present composition may also comprise other components commonly used in dermal formulations, e.g. antioxidants (e.g. alpha-tocopherol), preservatives, sodium edetate, pigments, skin soothing agents, skin healing agents and skin conditioning agents such as urea, allantoin or bisabolol, cf. *CTFA Cosmetic Ingredients Handbook*, $2^{nd}$ Ed., 1992.

The composition of the invention may be used in the treatment of psoriasis, sebopsoriasis, pustulosis palmoplantaris, dermatitis, ichtyosis, rosacea and acne and related skin diseases by topically administering an effective amount of a composition according to the invention to a patient in need of such treatment. Said method preferably comprises topical administration once or twice a day of a therapeutically sufficient dosage of said composition. To that end, the composition according to the invention preferably contains about 0.001-0.5 mg/g, preferably about 0.002-0.25 mg/g, in particular 0.005-0.05 mg/g, of the vitamin D derivative or analogue. It is envisaged that the present composition may advantageously been used for maintenance treatment of these dermal diseases, i.e. continued treatment after the disappearance of visible symptoms to delay the recurrence of symptoms.

To provide a more effective treatment of psoriasis and other dermal conditions in the acute phase, it may be desirable to include one or more additional therapeutically active ingredients in the composition. Examples of such additional active ingredients include, but are not limited to, anti-inflammatory drugs such as corticosteroids, such as betamethasone and esters thereof, e.g. the valerate or dipropionate ester, clobetasol or esters thereof, such as the propionate, hydrocortisone or esters thereof, such as the acetate; non-steroidal anti-inflammatory drugs such as naproxen, indomethacin, diclofenac, ibuprofen, dexibuprofen, ketoprofen, flurbiprofen, piroxicam, tenoxicam, lornoxicam or nabumeton, phosphodiesterase 4 inhibitors or p38 MAP kinase inhibitors.

The invention is further illustrated by the following examples which are not in any way intended to limit the scope of the invention as claimed.

EXAMPLE 1

Compositions of the Invention

The compositions shown in Tables 1a and 1b below were prepared by initially mixing the surfactant (Cremophor EL, Labrasol, polysorbate 80 or cetomacrogol 1000) with the co-solvent (ethanol or isopropanol), dissolving calcipotriol monohydrate in the mixture and finally adding the mixture to the aqueous buffer solution adjusted to pH 8.0 and glycerol (when included). The resulting dispersion was then mixed with a mixture of paraffins, emulsifier (polyoxyethylene stearyl ether), DL-α-tocopherol and sodium edetate.

TABLE 1a

Compositions A-F according to the invention

| Composition mg/g | A | B | C | D | E | F |
|---|---|---|---|---|---|---|
| Calcipotriol monohydrate | 0.050 | 0.050 | 0.050 | 0.050 | 0.050 | 0.050 |
| Disodium hydrogen phosphate | 0.65 | 0.65 | 0.65 | 0.65 | 0.26 | 0.26 |
| Paraffin, liquid | 50 | 50 | 50 | 50 | 50 | 50 |
| Polyoxyethylene stearyl ether | 50 | 50 | 50 | 50 | 50 | 50 |
| Water, purified | 65 | 65 | 65 | 65 | 65 | 65 |
| Cetomacrogol 1000 | 15 | 15 | | | | |
| Cremophor EL | | | 15 | 15 | | |
| Labrasol | | | | | 15 | 15 |
| Ethanol | 20 | 20 | | | 20 | 20 |
| Isopropanol | | | 20 | 20 | | |
| Glycerol 85% | | 65 | | 65 | | 65 |
| Sodium edetate | 0.065 | 0.065 | 0.065 | 0.065 | 0.065 | 0.065 |
| DL-α-tocopherol | 0.02 | 0.02 | 0.02 | 0.02 | 0.02 | 0.02 |
| Paraffin, white soft | up to 1 g | up to 1 g | up to 1 g | up to 1 g | up to 1 g | up to 1 g |

TABLE 1b

Compositions G-L of the invention

| Composition mg/g | G | H | I | J | K | L |
|---|---|---|---|---|---|---|
| Calcipotriol monohydrate | 0.050 | 0.050 | 0.050 | 0.050 | 0.050 | 0.050 |
| Disodium hydrogen phosphate | 0.65 | 0.65 | 0.65 | 0.65 | 0.65 | 0.65 |
| Paraffin, liquid | 50 | 50 | 50 | 50 | 50 | 50 |
| Polyoxyethylene stearyl ether | 50 | 50 | 50 | 50 | 50 | 50 |
| Water, purified | 65 | 65 | 65 | 65 | 65 | 65 |
| Labrasol | 15 | 15 | | | | |
| Polysorbate 80 | | | 15 | 15 | 15 | 15 |
| Ethanol | | | 20 | 20 | | |
| Isopropanol | 20 | 20 | | | 20 | 20 |
| Glycerol 85% | | 65 | | 65 | | 65 |
| Sodium edetate | 0.065 | 0.065 | 0.065 | 0.065 | 0.065 | 0.065 |
| DL-α-tocopherol | 0.02 | 0.02 | 0.02 | 0.02 | 0.02 | 0.02 |
| Paraffin, white soft | up to 1 g | up to 1 g | up to 1 g | up to 1 g | up to 1 g | up to 1 g |

TABLE 2

Compositions M and N of the invention

| Composition mg/g | M | N |
|---|---|---|
| Calcipotriol monohydrate | 0.050 | 0.050 |
| Disodiumhydrogenphosphate | 0.65 | |
| Triethanolamine | | 1 |
| Paraffin, liquid | 50 | 50 |
| Polyoxyethylene stearyl ether | 50 | 50 |
| Water, purified | 65 | 65 |
| Polysorbate 80 | 15 | |
| Labrasol | | 15 |
| Ethanol | 20 | 20 |
| Glycerol 85% | | 65 |
| Sodium edetate | 0.065 | |
| DL-α-tocopherol | 0.02 | 0.02 |
| Petrolatum Jelly White (Sonnecone DM1) | 699.2 | 634.2 |
| Microcrystalline wax (Multiwax 180 MH) | 100 | 100 |

Compositions M and N were prepared essentially as described above for compositions A-L with the exception that a mixture of Petrolatum Jelly White (Sonnecone DM1) and microcrystalline wax was used instead of white soft paraffin and, as regards composition N, triethanolamine was added to the aqueous phase instead of disodium hydrogen phosphate.

EXAMPLE 2

Solubility of Calcipotriol in Solvent/Surfactant Mixtures in Aqueous Buffer

Cetomacrogol 1000 in Combination with Ethanol

The solubility, at 25° C., of calcipotriol monohydrate, determined as calcipotriol, in aqueous buffer pH 7.4 containing cetomacrogol 1000 as surfactant and ethanol as co-solvent is shown in Table 3 below. It appears from Table 3 that there is a small synergistic effect of the combination of cetomacrogol 1000 and ethanol on the solubility of calcipotriol in the aqueous phosphate buffer solution, i.e. the observed solubility of calcipotriol in aqueous phosphate buffer containing 15% cetomacrogol 1000 and 20% ethanol is 1468 μg/g, which is approximately 1.4 times higher than the sum of the solubility of calcipotriol in aqueous phosphate buffer containing either 15% cetomacrogol 1000 or 20% ethanol (1049 μg/g+2.33 μg/g=1051 μg/g), see FIG. 1.

TABLE 3

Solubility of calcipotriol (as μg/g) in aqueous vehicles using cetomacrogol 1000 as surfactant and ethanol as co-solvent at 25° C.

| Vehicle | Solubility μg/g |
|---|---|
| Phosphate buffer pH 7.4:ethanol (80:20) | 2.33 |
| Phosphate buffer pH 7.4:cetomacrogol 1000 (85:15) | 1049 |
| Phosphate buffer pH 7.4:cetomacrogol 1000:ethanol (65:15:20) | 1468 |

Labrasol in Combination with Ethanol

The solubility, at 25° C., of calcipotriol monohydrate, determined as calcipotriol, in aqueous buffer pH 7.4 containing Labrasol as surfactant and ethanol as co-solvent is shown in Table 4 below. It appears from Table 4 that there is a pronounced synergistic effect of the combination of Labrasol and ethanol on the solubility of calcipotriol in the aqueous phosphate buffer solution, i.e. the observed solubility of calcipotriol in aqueous phosphate buffer containing 15% Labrasol and 20% ethanol is 1059 µg/g, which is approximately 3.6 times higher than the sum of the solubility of calcipotriol in aqueous phosphate buffer containing either 15% Labrasol or 20% ethanol (292 µg/g+2.33 µg/g=294 µg/g), see FIG. 2.

TABLE 4

Solubility of calcipotriol (as µg/g) in aqueous vehicles using Labrasol as surfactant and ethanol as co-solvent at 25° C.

| Vehicle | Solubility µg/g |
|---|---|
| Phosphate buffer pH 7.4:ethanol (80:20) | 2.33 |
| Phosphate buffer pH 7.4:Labrasol (85:15) | 292 |
| Phosphate buffer pH 7.4:Labrasol:ethanol (65:15:20) | 1059 |

Labrasol in Combination with Isopropanol

The solubility, at 25° C., of calcipotriol monohydrate, determined as calcipotriol, in aqueous buffer pH 7.4 containing Labrasol as surfactant and isopropanol as co-solvent is shown in Table 5 below. It appears from Table 5 that there is a pronounced synergistic effect of the combination of Labrasol and isopropanol on the solubility of calcipotriol in the aqueous phosphate buffer solution, i.e. the observed solubility of calcipotriol in aqueous phosphate buffer containing 15% Labrasol and 20% isopropanol is 1508 µg/g, which is approximately 4.9 times higher than the sum of the solubility of calcipotriol in aqueous phosphate buffer containing either 15% Labrasol or 20% isopropanol (292 µg/g+17.2 µg/g=309 µg/g), see FIG. 3.

TABLE 5

Solubility of calcipotriol (as µg/g) in aqueous vehicles using Labrasol as surfactan and isopropanol as co-solvent at 25° C.

| Vehicle | Solubility µg/g |
|---|---|
| Phosphate buffer pH 7.4:isopropanol (80:20) | 17.2 |
| Phosphate buffer pH 7.4:Labrasol (85:15) | 292 |
| Phosphate buffer pH 7.4:Labrasol:isopropanol (65:15:20) | 1508 |

Polysorbate 80 in Combination with Ethanol

The solubility, at 25° C., of calcipotriol monohydrate, determined as calcipotriol, in aqueous buffer pH 7.4 containing polysorbate (Tween) 80 as surfactant and ethanol as co-solvent is shown in Table 6 below. It appears from Table 6 that there is a synergistic effect of the combination of polysorbate 80 and ethanol on the solubility of calcipotriol in the aqueous phosphate buffer solution, i.e. the observed solubility of calcipotriol in aqueous phosphate buffer containing 15% polysorbate 80 and 20% ethanol is 740 µg/g, which is approximately 2.0 times higher than the sum of the solubility of calcipotriol in aqueous phosphate buffer containing either 15% polysorbate 80 or 20% ethanol (360 µg/g+2.33 µg/g=362 µg/g), see FIG. 4.

TABLE 6

Solubility of calcipotriol (as µg/g) in aqueous vehicles using polysorbate 80 as surfactant and ethanol as co-solvent at 25° C.

| Vehicle | Solubility µg/g |
|---|---|
| Phosphate buffer pH 7.4:ethanol (80:20) | 2.33 |
| Phosphate buffer pH 7.4:polysorbate 80 (85:15) | 360 |
| Phosphate buffer pH 7.4:polysorbate 80:ethanol (65:15:20) | 740 |

The results presented in Tables 3-6 below show that a higher solubility of calcipotriol monohydrate may be achieved in an aqueous solution by the synergistic action of a co-solvent combined with a surfactant instead of using either the co-solvent alone or the surfactant alone. This implies that a lower amount of the combination may be used to achieve the same solubility of calcipotriol monohydrate than when either solvent is used on its own.

EXAMPLE 3

Penetration Studies

To investigate the skin penetration and permeation of calcipotriol from compositions of the invention, a skin diffusion experiment was conducted. Full thickness skin from pig ears was used in the study. The ears were kept frozen at −18° C. before use. On the day prior to the experiment the ears were placed in a refrigerator (5±3° C.) for slow defrosting. On the day of the experiment, the hairs were removed using a veterinary hair trimmer. The skin was cleaned for subcutaneous fat using a scalpel and two pieces of skin were cut from each ear and mounted on Franz diffusion cells in a balanced order.

Static Franz-type diffusion cells with an available diffusion area of 3.14 cm$^2$ and receptor volumes ranging from 8.6 to 11.1 ml were used in substantially the manner described by T. J. Franz, "The finite dose technique as a valid in vitro model for the study of percutaneous absorption in man", in *Current Problems in Dermatology*, 1978, J. W. H. Mall (Ed.), Karger, Basel, pp. 58-68. The specific volume was measured and registered for each cell. A magnetic bar was placed in the receptor compartment of each cell. After mounting the skin, physiological saline (35° C.) was filled into each receptor chamber for hydration of the skin. The cells were placed in a thermally controlled water bath which was placed on a magnetic stirrer set at 400 rpm. The circulating water in the water baths was kept at 35±1° C. resulting in a temperature of about 32° C. on the skin surface. After one hour the saline was replaced by receptor medium, 0.04 M isotonic phosphate buffer, pH 7.4 (35° C.), containing 4% bovine serum albumin. Sink conditions were maintained at all times during the period of the study, i.e. the concentration of the active compounds in the receptor medium was below 10% of the solubility of the compounds in the medium.

The in vitro skin permeation of each test composition was tested in 6 replicates (i.e. n=6). Each test composition was applied to the skin membrane at 0 hours in an intended dose of 4 mg/cm$^2$. A glass spatula was used for the application, and the residual amount of the composition was determined so as to give the amount of the composition actually applied on the skin.

The skin penetration experiment was allowed to proceed for 21 hours. Samples were then collected from the following compartments:

The stratum corneum was collected by tape stripping 10 times using D-Squame® tape (diameter 22 mm, CuDerm Corp., Dallas, Tex., USA). Each tape strip is applied to the test area using a standard pressure for 5 seconds and removed from the test area in one gentle, continuous move. For each repeated strop, the direction of tearing off was varied. The viable epidermis and dermis was then sampled from the skin in a similar fashion.

Samples (1 ml) of the receptor fluid remaining in the diffusion cell were collected and analysed.

The concentration of calcipotriol in the samples were determined by LC mass spectrometry.

Figure 5B:
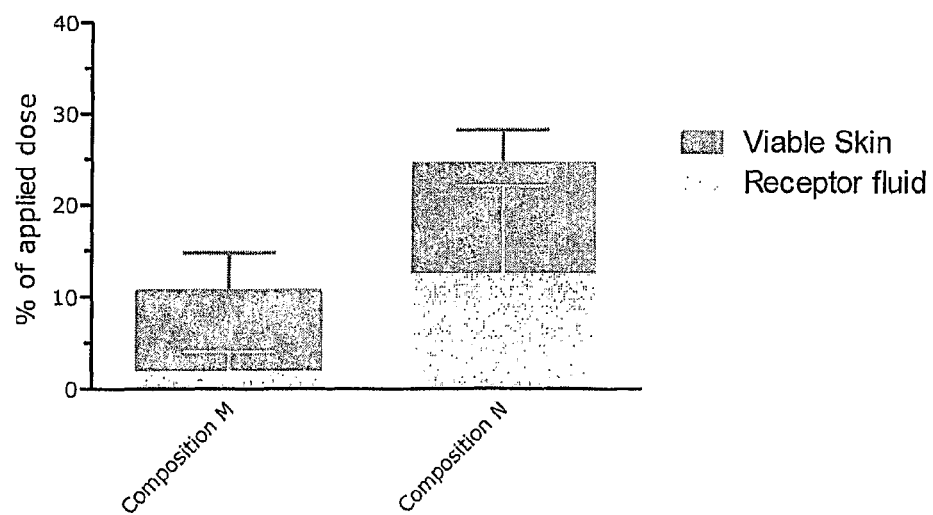

The results appear from FIGS. 5a and 5b below which show the amount of calcipotriol found in viable skin (dermis and epidermis) and receptor fluid in % of the applied dose. An excellent penetration and permeation profile was found for compositions of the invention, in particular those containing Labrasol as the surfactant component.

EXAMPLE 4

Biological Activity of the Compositions

Figure 6:
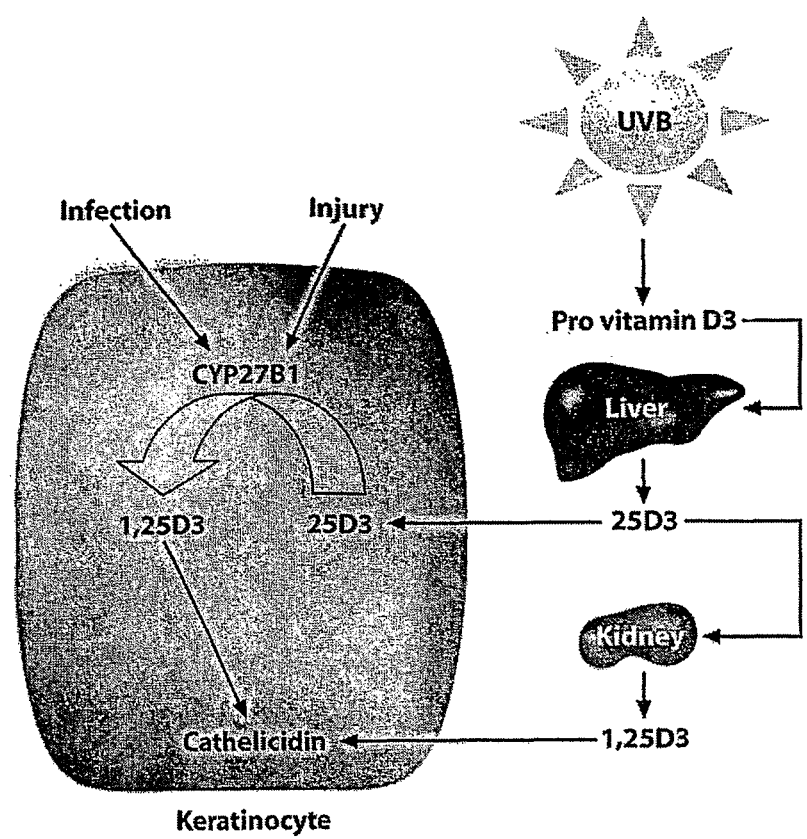
FIG. 6 is a schematic representation of the activation of the gene encoding cathelicidin by vitamin $D_3$ in human keratinocytes. The mechanism of cathelicidin gene activation is used in a biological assay using reconstructed human epidermis (human keratinocytes cultured so as to form the epidermal layers characteristic of human skin) on which calcipotriol-containing compositions of the invention are applied to activate cathelicidin as described in detail in Example 4 below.

As shown in FIG. 6 below, cathelicidin is an antimicrobial peptide expressed in human keratinocytes. The expression of cathelicidin is strongly induced on infection of the skin or disruption of the skin barrier. In psoriasis, the level of cathelicidin is increased in lesional skin of psoriasis patients. It has been found that the expression of the gene encoding cathelicidin may be induced by vitamin $D_3$ or vitamin D analogues such as calcipotriol (cf. T T Wang et al, *J. Immunol.* 173(5), 2004, pp. 2909-2912; J Schauber et al., *Immunology* 118(4), 2006, pp. 509-519; Schauber and Gallo, *J. Allergy Clin Immunol* 122, 2008, pp. 261-266; M. Peric et al., PloS One 4(7), 22 Jul. 2009, e6340) through binding to the vitamin D receptor. This finding has been utilized to develop an assay in which the uptake and biological activity of calcipotriol in human keratinocytes from the tested compositions has been determined by measuring the level of induction of the gene encoding cathelicidin.

In the assay, compositions A, B, C, F, G, I, J, K, L prepared as described in Example 1 above were applied topically in triplicate on reconstructed human epidermis consisting of normal human keratinocytes cultured for 12 days on 0.5 cm² polycarbonate filters (available from SkinEthic® Laboratories, Nice, France) in an amount of 10 μl. The tissue was treated for two days followed by separation of the epidermis from the polycarbonate filter and snap-frozen in liquid nitrogen. RNA was extracted from the cells and cDNA synthesized by conventional procedures. Quantitative real-time PCR (qPCR) was then performed using the following assays from Applied Biosystems: CAMP Hs0018038_ml and GAPDH Hs99999905_ml. The expression levels of cathelicidin were normalized to GAPDH and a relative quantification was made by comparison with Daivonex® ointment.

The results appear from Table 7 below.

TABLE 7

| Composition | Fold activation[1] |
| --- | --- |
| Daivonex ® ointment | 1.0 |
| composition A | 1.9 |
| composition B | 9.4/6.4 |
| composition C | 3.5 |
| composition F | 2.1 |
| composition G | 10.9 |
| composition I | 4.1 |
| composition J | 5.2 |
| composition K | 6.6 |
| composition L | 1.9 |

[1]relative to Daivonex ® ointment

The results presented in Table 7 show that the compositions of the invention result in higher activation of the target gene, i.e. they may have a higher biological activity in vivo than the marketed ointment.

EXAMPLE 5

Local Tolerance Study in Minipigs

The local tolerability of compositions B, G, M and N of Example 1 was assessed when administered daily by dermal application to minipigs for 4 weeks. Daivonex® ointment was used for comparison. Each day the animals were exposed to the test items for 8 hours.

The study was conducted in 10 female Göttingen SPF minipigs. Each animal had 6 application sites and received a volume of 250 mg test formulation per application site. Clinical signs were recorded daily and skin reactions at the application sites were scored once daily prior to start of dosing and, furthermore, on the day of necropsy in relation to erythema and oedema. Food consumption was recorded daily and the body weight weekly. At the end of the treatment period a gross necropsy was performed on all animals and skin samples were collected from histopathological examination.

The results show that no adverse treatment-related clinical signs were observed during the study though grade 1-2 skin reactions (erythema) were observed. Except for composition G, the erythemas were less pronounced than those observed for Daivonex® ointment. The results imply that compositions of the invention may be better tolerated in human patients than Daivonex® ointment.

The invention claimed is:

1. A stable topical composition for cutaneous application which is an oil-in-water-in-oil emulsion comprising 5-10% by weight of an aqueous phase containing, dispersed therein, a lipophilic phase consisting essentially of:
    (a) calcipotriol or calcipotriol monohydrate in dissolved form;
    (b) a non-ionic surfactant selected from the group consisting of polyoxyl glycerides, polyoxyethylene alkyl ethers, and polysorbates in an amount of 1-3% by weight of the composition; and
    (c) a lower alkanol co-solvent selected from the group consisting of ethanol and isopropanol in an amount of 1-3% by weight of the composition;
    provided that, when the co-solvent is ethanol, the non-ionic surfactant is a polysorbate or a polyoxyethylene alkyl ether, and when the co-solvent is isopropanol, the non-ionic surfactant is a polyoxyl glyceride or a polysorbate;
    said aqueous phase being dispersed in a pharmaceutically acceptable anhydrous lipophilic carrier or vehicle comprising a paraffin in an amount of 80-93% by weight of the composition.

2. The composition according to claim 1, wherein the non-ionic surfactant is a polyethylene glycol $C_{6-20}$ fatty acid glyceride selected from the group consisting of caprylocaproyl PEG glyceride, lauroyl PEG glyceride, linoeoyl PEG glyceride, oleoyl PEG glyceride and stearoyl PEG glyceride, a polyoxyethylene $C_{8-20}$ alkyl ether selected from the group consisting of PEG monocetyl ether, PEG monolauryl ether, PEG monooleyl ether and PEG monostearyl ether, or a polysorbate selected from the group consisting of polysorbate 20, 40, 60 and 80.

3. The composition according to claim 1 wherein the non-ionic surfactant is polyethylene glycol 8 caprylic/capric glyceride or polyethylene glycol 6 caprylic/capric glyceride.

4. The composition according to claim 1, wherein the co-solvent is ethanol and the non-ionic surfactant is polyethylene glycol 8caprylic/capric glyceride, polysorbate 80 or PEG monocetyl ether, or wherein the co-solvent is isopropanol and the non-ionic surfactant is polyoxyl castor oil, polyethylene glycol 8 caprylic/capric glyceride or polysorbate 80.

5. A composition according to claim 1, wherein the carrier comprises at least one paraffin selected from paraffins consisting of hydrocarbons with chain lengths from $C_5$ to $C_{60}$, the chain lengths peaking at $C_{14-16}$, $C_{18-22}$, $C_{20-22}$, $C_{20-26}$, $C_{28-40}$, and $C_{40-44}$ as determined by gas chromatography and mixtures thereof.

6. A composition according to claim 1, further comprising a viscosity-increasing ingredient.

7. A composition according to claim 6, wherein the viscosity-increasing ingredient is a wax.

8. A composition according to claim 1, further comprising a silicone wax or a volatile silicone oil.

9. A composition according to claim 8, wherein the volatile silicone oil is cyclomethicone or dimethicone.

10. A composition according to claim 1, further comprising an anti-irritant compound.

11. A composition according to claim 10, wherein the anti-irritant compound is glycerol, butylene glycol, sorbitol, sucrose, saccharin, menthol or nicotinamide.

12. A composition according to claim 1, further comprising a compound capable of neutralizing acidic impurities detrimental to the chemical stability of the calcipotriol or calcipotriol monohydrate in the composition.

13. A composition according to claim 12, wherein said compound is a tertiary amine such as triethanol amine, trometamol, monoethanolamine or diethanolamine.

14. A composition according to claim 1 comprising about 0.001-0.5 mg/g of the calcipotriol or calcipotriol monohydrate.

15. A composition according to claim 1 comprising:

| | |
|---|---|
| 0.003-0.008% w/w | calcipotriol as monohydrate |
| 1-3% w/w | polysorbate 80 |
| 1-3% w/w | ethanol |
| 3-8% w/w | polyoxyethylene stearyl ether |
| 5-10% w/w | water |
| 80-93% w/w | paraffin carrier. |

16. A composition according to claim 1 comprising:

| | |
|---|---|
| 0.003-0.008% w/w | calcipotriol as monohydrate |
| 1-3% w/w | polyethylene glycol monocetyl ether |
| 1-3% w/w | ethanol |
| 3-8% w/w | polyoxyethylene stearyl ether |
| 5-10% w/w | water |
| 80-93% w/w | paraffin carrier. |

17. A composition according to claim 1 comprising:

| | |
|---|---|
| 0.003-0.008% w/w | calcipotriol as monohydrate |
| 1-3% w/w | polyethylene glycol 8 caprylic/capric glyceride |
| 1-3% w/w | isopropanol |
| 3-8% w/w | polyoxyethylene stearyl ether |
| 5-10% w/w | water |
| 80-93% w/w | paraffin carrier. |

18. A composition according to claim 1 comprising:

| | |
|---|---|
| 0.003-0.008% w/w | calcipotriol as monohydrate |
| 1-3% w/w | polyoxyl castor oil |
| 1-3% w/w | isopropanol |
| 3-8% w/w | polyoxyethylene stearyl ether |
| 5-10% w/w | water |
| 80-93% w/w | paraffin carrier. |

19. A composition according to claim 1 comprising:

| | |
|---|---|
| 0.003-0.008% w/w | calcipotriol as monohydrate |
| 1-3% w/w | polysorbate 80 |
| 1-3% w/w | isopropanol |
| 3-8% w/w | polyoxyethylene stearyl ether |
| 5-10% w/w | water |
| 80-93% w/w | paraffin carrier. |

20. A composition according to claim 1, further comprising one or more additional therapeutically active ingredients.

21. A composition according to claim 20, wherein such additional active ingredients are selected from the group consisting of corticosteroids and non-steroidal anti-inflammatory drugs.

22. A composition according to claim 1 for use in the treatment of a dermal disease or condition.

23. The composition of claim 22, wherein the dermal disease or condition is psoriasis, sebopsoriasis, pustulosis palmoplantaris, dermatitis, ichtyosis, rosacea or acne.

24. The composition according to claim 1, wherein the non-ionic surfactant is present in a total concentration of from about 1.2% by weight to about 2% by weight of the composition.

25. A composition according to claim 1 comprising about 0.002-0.25 mg/g of the calcipotriol or calcipotriol monohydrate.

26. A composition according to claim 1 comprising 0.005-0.05 mg/g of the calcipotriol or calcipotriol monohydrate.

27. A composition according to claim 20, wherein such additional active ingredients are selected from the group consisting of betamethasone and esters thereof, clobetasol and esters thereof, hydrocortisone and esters thereof, naproxen, indomethacin, diclofenac, ibuprofen, dexibuprofen, ketoprofen, flurbiprofen, piroxicam, tenoxicam, lornoxicam or nabumeton, phosphodiesterase 4 inhibitors and p38 MAP kinase inhibitors.

28. A composition according to claim 27, wherein the betamethasone esters include valerate and dipropionate esters, the clobetasol ester is the propionate ester, and the hydrocortisone ester is the acetate ester.

* * * * *